United States Patent [19]
Vonderhaar et al.

[11] Patent Number: 6,033,199
[45] Date of Patent: Mar. 7, 2000

[54] APPARATUS FOR FORMING AN INTERMITTENT STREAM OF PARTICLES FOR APPLICATION TO A FIBROUS WEB

[75] Inventors: Michael Francis Vonderhaar; James Michael Fleming, both of Cincinnati, Ohio

[73] Assignee: The Procter & Gamble Company, Cincinnati, Ohio

[21] Appl. No.: 08/526,657

[22] Filed: Sep. 11, 1995

Related U.S. Application Data

[63] Continuation of application No. 08/139,249, Oct. 19, 1993, abandoned.

[51] Int. Cl.[7] .................................................... B05C 5/00
[52] U.S. Cl. ........................ 425/81.1; 425/82.1; 118/301
[58] Field of Search .................................. 425/80.1, 81.1, 425/83.1, 82.1; 156/62.2, 62.4; 118/301; 19/304

[56] References Cited

U.S. PATENT DOCUMENTS

| | | | |
|---|---|---|---|
| 2,672,842 | 3/1954 | Winters et al. | 118/2 |
| 3,192,796 | 7/1965 | Peeps et al. | 74/568 |
| 3,581,706 | 6/1971 | Rasmussen | 118/312 |
| 3,617,331 | 11/1971 | Illsley et al. | 117/33.3 |
| 3,888,257 | 6/1975 | Cook et al. | 128/296 |
| 4,087,506 | 5/1978 | Cook et al. | 264/112 |
| 4,212,216 | 7/1980 | Ives | 156/62.4 |
| 4,269,874 | 5/1981 | Pryor et al. | 427/282 |
| 4,388,056 | 6/1983 | Lee et al. | 425/83.1 |
| 4,551,191 | 11/1985 | Kock et al. | 156/276 |
| 4,583,486 | 4/1986 | Miller | 118/308 |
| 4,610,678 | 9/1986 | Weisman et al. | 604/368 |
| 4,764,325 | 8/1988 | Angstadt | 264/113 |
| 4,765,780 | 8/1988 | Angstadt | 406/123 |
| 4,800,102 | 1/1989 | Takada | 427/197 |
| 4,888,231 | 12/1989 | Angstadt | 428/213 |
| 4,902,559 | 2/1990 | Eschwey et al. | 156/62.4 |
| 4,904,440 | 2/1990 | Angstadt | 264/517 |
| 4,908,175 | 3/1990 | Angstadt | 264/113 |
| 4,927,346 | 5/1990 | Kaiser et al. | 425/81.1 |
| 4,927,582 | 5/1990 | Bryson | 264/113 |
| 4,931,243 | 6/1990 | Henschel et al. | 425/83.1 |
| 5,017,324 | 5/1991 | Kaiser et al. | 264/510 |
| 5,028,224 | 7/1991 | Pieper et al. | 425/80.1 |
| 5,064,484 | 11/1991 | Craig et al. | 425/81.1 |
| 5,102,585 | 4/1992 | Pieper et al. | 264/37 |
| 5,111,552 | 5/1992 | Lauren et al. | 156/62.4 |
| 5,156,902 | 10/1992 | Pieper et al. | 428/206 |
| 5,213,817 | 5/1993 | Pelley | 425/81.1 |
| 5,415,717 | 5/1995 | Perneborn | 156/276 |
| 5,429,788 | 7/1995 | Ribble et al. | 264/510 |

FOREIGN PATENT DOCUMENTS

| | | | |
|---|---|---|---|
| 2942163 | 4/1981 | Germany | 425/80.1 |
| 2 150 033 | 6/1985 | United Kingdom . | |

*Primary Examiner*—Allan R. Kuhns
*Attorney, Agent, or Firm*—Gerry S. Gressel; Larry L. Huston; E. Kelly Linman

[57] ABSTRACT

The present invention provides an apparatus for applying discrete particles of absorbent material to a predetermined location on a fibrous web. The apparatus comprises a continuously rotating mask, and a means for directing a supply stream of absorbent particles to form an acute included angle with a diverting surface on the rotating mask. The mask diverting surface splits the supply stream of absorbent particles into a first intermittent stream passing through the mask and a second intermittent stream deflected by the diverting surface. The absorbent particles in one of the first and second intermittent streams is directed to the fibrous web.

9 Claims, 7 Drawing Sheets

APPARATUS FOR FORMING AN INTERMITTENT STREAM OF PARTICLES FOR APPLICATION TO A FIBROUS WEB

This is a continuation of application Ser. No. 08/139,249, filed on Oct. 19, 1993, now abandoned.

FIELD OF THE INVENTION

This invention is related to a method and apparatus for forming fibrous webs having a predetermined distribution of particulate material. More particularly, the invention is related to forming an intermittent stream of particulate material for application to a fibrous web.

BACKGROUND OF THE INVENTION

Absorbent articles such as disposable diapers, incontinence pads, and catamenial napkins generally include an absorbent core for receiving and holding body exudates. The absorbent core typically includes a fibrous web, which can be a nonwoven, airlaid web of natural or synthetic fibers. A class of particulate absorbent materials known as superabsorbent polymers or absorbent gelling materials can be incorporated in the fibrous web to improve the absorption and retention characteristics of the fibrous web.

Because absorbent gelling materials are generally significantly more expensive than readily available natural or synthetic fiber materials (e.g., cellulose fibers), it is advantageous to reduce the quantity of absorbent gelling material in the core. Rather than uniformly reducing such particles throughout the entire core, it is desirable to distribute the particles in the absorbent core in a predetermined manner so that the particles are located where they will be most effective in acquiring and retaining body exudates.

Various techniques have been developed to distribute and locate absorbent materials on or within a fibrous substrate. U.S. Pat. No. 4,800,102 issued to Takada discloses applying a powder to the top surface of a substrate by spraying powder through an opening in a rotating disc member. Powder not passing through the opening is shown to be supported on a horizontal surface of the disc as the disc rotates, and is subsequently scraped from the disc by a scraper into a receiving member below the scraper. Powder not removed by the scraper is removed by a vacuum sucker positioned above the disc. Such an arrangement is disadvantageous because it requires powder material to accumulate on the disc. The arrangement requires a relatively complicated scraper and vacuum device to remove powder from the disc. Centrifugal forces may cause some of the accumulated powder to be flung from the disc, thereby complicating powder recycling. Powder accumulating on the disc prior to removal may also cause rotary imbalance and vibration of the disc, especially if the disc is rotated at the relatively high speeds desirable for cost effective production rates. Further, the powder material is shown to be directed generally perpendicular to the disc surface. Therefore, powder material may strike and bounce off of the disc in an unpredictable direction, thereby further complicating powder recycling.

U.S. Pat. No. 5,028,224 issued to Pieper et al. discloses pulsing and diverting mechanisms for producing an intermittent flow of absorbent particles. The diverting mechanism includes a flap which rotates about a pivot between a closed position and an open position to provide an intermittent quantity of particulate material. Such an arrangement is undesirable because operation of such a flap between the open and closed positions requires accelerating and decelerating the flap between two stationary positions. Operating such a reversing mechanism at high speeds can result in undesirable inertial forces in the mechanism, and complicates precise control of the definition of the pulse of the particulate material.

U.S. Pat. No. 5,213,817 issued to Pelley discloses a stream of powder material passing through a nozzle which is movable between first and second positions. A flow separator splits the stream into two intermittent streams as the nozzle is moved between the first and second positions. As in Pieper et al. above, such an arrangement is undesirable because operation of the nozzle between two positions requires accelerating and decelerating the nozzle between two stationary positions. Reversing the direction of motion of the nozzle at high speeds results in undesirable inertial forces, and complicates precise control of the definition of the pulse of particulate material.

Accordingly, it is an object of the present invention to provide an apparatus and method for applying discrete particles to a fibrous web. It is another object of the present invention to provide a pulse of discrete particles for application to a predetermined location on a fibrous web. Another object of the present invention is to provide a continuously rotating mask having a particle diverting surface forming an acute included angle with a supply stream of particles to split the stream of discrete particles into a first intermittent stream passing through the mask and a second intermittent stream deflected by the diverting surface.

SUMMARY OF THE INVENTION

The present invention comprises an apparatus for and method of applying discrete particles to a predetermined location on a fibrous web. The apparatus includes a conveyor for supporting and moving the fibrous web; a means for forming a supply stream of discrete particles; a mask moving continuously relative to the supply stream of particles; a diverting surface on the mask for splitting the supply stream of particles into a first intermittent stream passing through the mask and a second intermittent stream deflected by the diverting surface; a means for directing the supply stream of discrete particles to form an acute included angle with mask diverting surface; and a means for directing the discrete particles in one of the intermittent streams of particles to the fibrous web.

The apparatus can include a foraminous forming element for forming an airlaid fibrous web; means for forming an air-entrained flow of fibers; means for combining the flow of fibers with one of the first and second intermittent streams to form a combined stream comprising an intermittent stream of particles within a continuous stream of fibers; and means for directing the combined stream of fibers and particles to the forming element. In a preferred embodiment, the mask is supported for continuous rotation about an axis, and the supply stream of discrete particles forms an included angle of less than 45 degrees with the diverting surface.

The method preferably comprises the steps of:
a. providing an airlaying means having a foraminous forming element for forming a fibrous web;
b. providing an air-entrained stream of fibers;
c. providing an air-entrained supply stream of discrete particles;
d. providing a mask having a diverting surface;
e. continuously rotating the mask about an axis;
f. directing the supply stream of discrete particles to form an acute included angle with the diverting surface for splitting the stream of discrete particles into a first intermittent stream of particles passing through the mask and a second intermittent stream of particles deflected by the diverting surface;

g. combining the stream of fibers with one of the intermittent streams of particles to form a combined stream comprising an intermittent stream of particles within a continuous stream of fibers; and h. directing the combined stream of fibers and particles to the forming element of the airlaying means.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

While the present invention will be described in the context of providing airlaid fibrous webs for use as absorbent cores in disposable absorbent articles such as disposable diapers, the present invention may also be employed to provide absorbent webs for use in a number of other articles, including but not limited to incontinence briefs, disposable training pants, and sanitary napkins.

Figure 1:
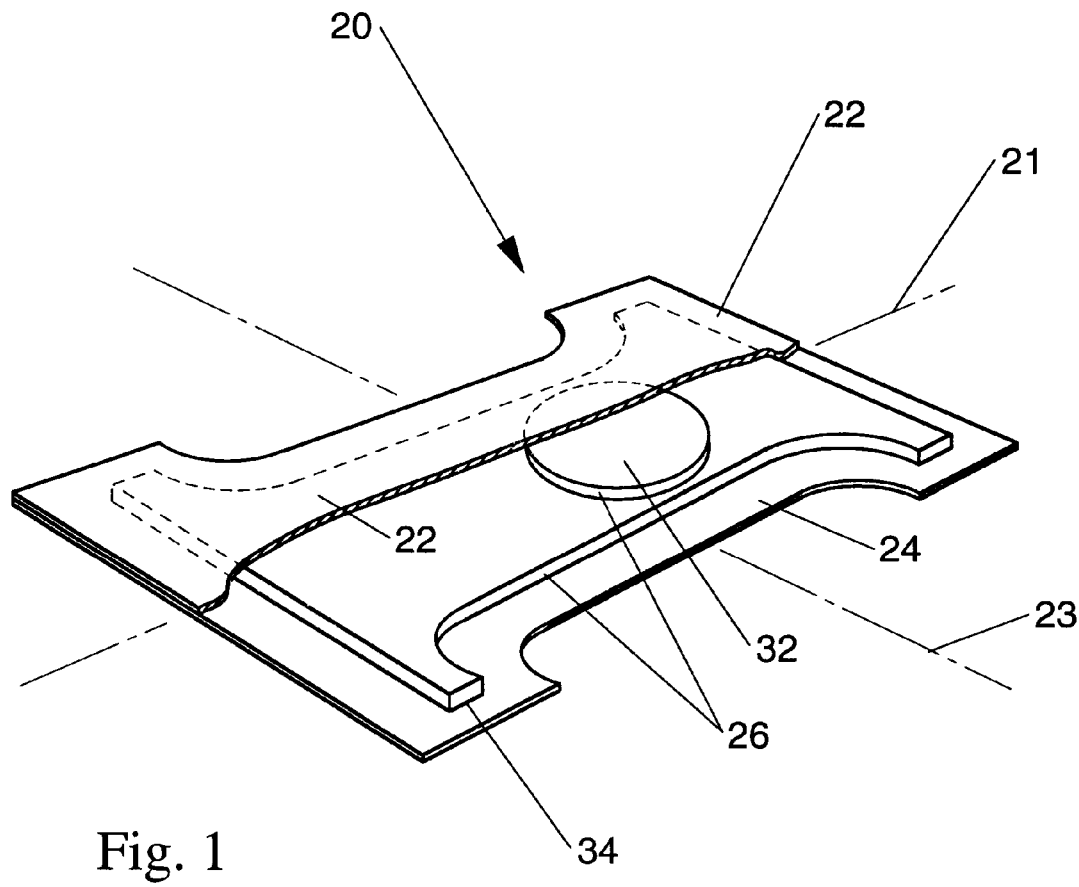
FIG. 1 is a perspective view of an absorbent article shown partially cut-away.

FIG. 1 shows a disposable diaper 20 having a liquid pervious topsheet 22, a liquid impervious backsheet 24, and an absorbent core 26 disposed between the topsheet 22 and the backsheet 24. Preferred constructions of such disposable diapers are described in U.S. Pat. No. 3,860,003 issued Jan. 14, 1975 to Buell and U.S. Pat. No. 5,151,092 issued Sept. 29, 1992 to Buell et al., which patents are incorporated herein by reference. The diaper 20 has a longitudinal centerline 21 and a lateral centerline 23. As used herein, the "longitudinal" dimension, direction, or axis of the diaper 20 is aligned front to back with respect to the wearer as the disposable absorbent article is worn. The "lateral" dimension, direction, or axis of the diaper 20 is perpendicular to the longitudinal direction and is sideways aligned as the diaper is worn.

The absorbent core 26 can include two or more components, such as a first insert core component 32 and a second shaped core component 34. Preferred absorbent core constructions are described in U.S. Pat. No. 4,673,402 issued Jun. 16, 1987 to Weisman et al.; U.S. Pat. No. 4,685,915 issued Aug. 11, 1987 to Hasse et al.; U.S. Pat. No. 4,834,735 issued May 30, 1989 to Alemany et al.; U.S. Pat. No. 5,217,445 issued Jun. 8, 1993 to Cook et al.; and U.S. Pat. No. 5,234,423 issued Aug. 10, 1993 to Alemany et al., which patents are incorporated herein by reference. The insert core component 32 serves to collect and distribute discharged body fluid, and can comprise a web of hydrophilic fiber material. The insert core component 32 can be free of particles of absorbent gelling material, or alternatively, can include an amount of particles of such material.

Figure 2:
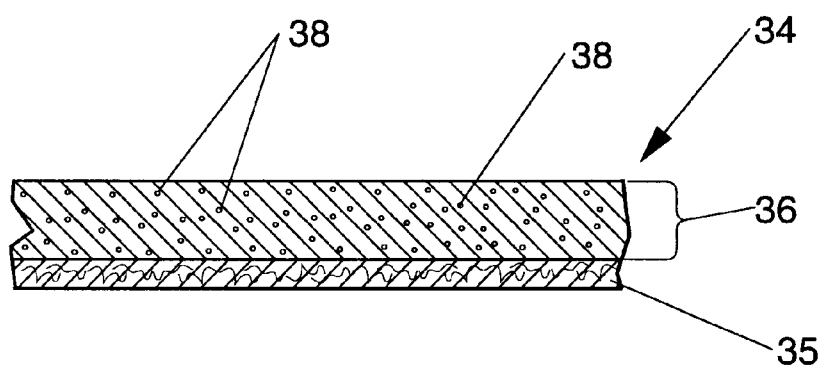
FIG. 2 is a cross-sectional view of an absorbent core having a dusting layer and a layer including discrete particles of absorbent material.

The shaped core component 34 absorbs discharged body fluids from the insert core component 32 and retains such fluids. As shown in FIGS. 1 and 2, the shaped core component 34 includes a thin dusting layer 35 of hydrophilic fiber material overlayed by a primary layer 36 of a combination of hydrophilic fiber material and discrete particles 38 of substantially water insoluble, fluid absorbing, absorbent gelling materials. While the dusting layer 35 is preferably a relatively thin layer of hydrophilic fiber material, it should be understood that the term "dusting layer" denotes a layer of the fibrous web and includes layers having any thickness.

There are several suitable absorbent gelling materials which can be used to form the discrete particles 38 in the shaped core component 34, such as silica gels or organic compounds such as crosslinked polymers. Particularly preferred absorbent gelling materials are hydrolyzed acrylonitrile grafted starch, acrylic acid grafted starch, polyacrylates and isobutylene maleic anhydride copolymers, or mixtures thereof U.S. Pat. No. Re. 32,649 reissued to Brandt et al. Apr. 19, 1988 is incorporated herein by reference for the purpose of showing suitable absorbent gelling materials.

Figure 3:
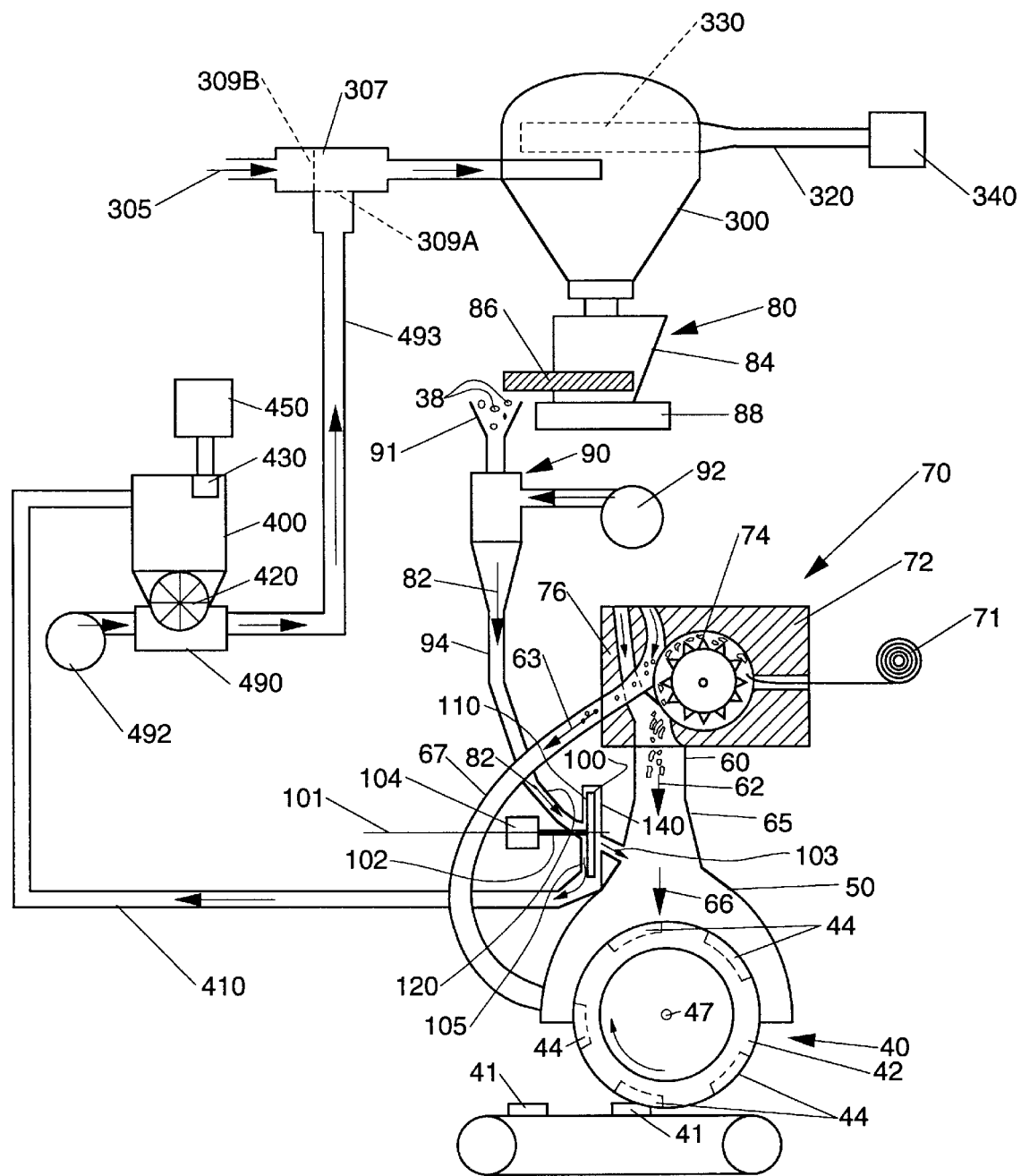
FIG. 3 is a schematic illustration of an apparatus according to one embodiment of the present invention having one particle recycling arrangement.

FIG. 3 shows an apparatus according to the present invention for forming an intermittent stream of absorbent gelling material particles and applying the intermittent stream of materials to a fibrous web. An intermittent stream of particles is a stream of particles having a particle flow rate which is periodically stopped or reduced. The apparatus includes a conveyor for supporting and moving a fibrous web, and preferably comprises an airlaying means such as a rotating drum-type airlaying module 40 having a foraminous forming element, such as a foraminous forming drum 42. Airlaying module 40 is suitable for forming an airlaid fibrous web 41, such as shaped core component 34.

The apparatus also preferably includes a means for forming an air-entrained stream of fibers 62, such as a disintegrator 70. The apparatus further includes a means for forming a supply stream 82 of discrete absorbent gelling material particles 38 such as a particle metering device 80 and an eductor 90.

The apparatus according to the present invention includes a mask 100 continuously moving with respect to the supply stream 82 of discrete particles. In a preferred embodiment the mask 100 is continuously rotated about an axis 101. The mask can be rotated about axis 101 by any suitable means, such as by a motor 104 and shaft 102 shown in FIG. 3. The mask 100 includes a diverting surface 110 for splitting the supply stream 82 of discrete particles into a first intermittent stream 103 of particles passing through the mask 100 and a second intermittent stream 105 of particles deflected by the diverting surface 110.

The apparatus according to the present invention also includes a means for directing the supply stream 82 of discrete particles to form an acute included angle A (FIG. 5) with the diverting surface 110. The means for directing the supply stream 82 to form an acute included angle A with the diverting surface 110 can include a mask delivery nozzle 120, shown in FIGS. 3, 4, 5, and 6. The apparatus can further include a means for combining the stream of fibers 62 with the first intermittent stream 103, such as a diverging duct 65, to form a combined stream 66 comprising an intermittent stream of particles within a continuous stream of fibers. A means for directing the combined stream 66, such as a drum hood 50, directs the combined stream 66 to the foraminous forming element 42 of the airlaying apparatus 40.

Referring to the components in FIG. 3 in more detail, the disintegrator 70 can include a rotary element 74 enclosed in a housing 72. The disintegrator 70 receives a fibrous sheet material 71 capable of being separated into individual fibers. The fibrous sheet material 71 can include synthetic and/or natural fibers, and preferably comprises cellulosic fibers. The rotary element 74 can be continuously driven in the direction shown in FIG. 3. Teeth on the rotary element 74 separate the individual fibers of the sheet material 71 as the sheet material 71 is fed into the disintegrator 70.

The disintegrator 70 can include splitter chute 76 for forming multiple streams of air-entrained fibers from the individual fibers separated by the rotary element 74. The splitter chute 76 can be directly or indirectly joined to or disposed within the housing 70. The splitter chute 76 provides the air-entrained stream of fibers 62, as well as a dusting layer air-entrained steam of fibers 63 for forming the dusting layer 35 shown in FIG. 2. The air-entrained stream of fibers 62 is carried from the splitter chute 76 by conduit 60, and the dusting layer air-entrained stream of fibers 63 is carried from the splitter chute 76 by dusting layer conduit 67.

U.S. Pat. Nos. 4,908,175 and 4,765,780, issued Mar. 13, 1990 and Aug. 23, 1988, respectively, to Angstadt et al., are incorporated herein by reference for the purpose of showing the construction of a suitable disintegrator 70 and splitter chute 76 for providing the air-entrained stream of fibers 62 and the dusting layer air-entrained stream of fibers 63. However, it will be understood by those skilled in the art that other apparatus for separating a roll or mat of fibrous material into individual fibers, including but not limited to hammermills, fiberizers, picker rolls, and lickerin rolls, may be used to provide the air-entrained streams of fibers 62 and 63.

The airlaying module 40 includes the rotating foraminous forming drum 42 on which the fibrous webs 41 can be formed. The foraminous forming drum 42 can include a plurality of formation cavities 44 circumferentially spaced about the periphery of the forming drum 42. Five formation cavities 44 are shown in FIG. 3, with each formation cavity 44 having a circumferential span of about seventy-two degrees. The forming drum 42 is rotated by a motor 45 (FIG. 10) or other suitable device. The forming drum 42 rotates in the direction shown in FIG. 3 such that fibers in the dusting layer air-entrained stream of fibers 63 are first deposited in the formation cavities 44 to form the dusting layer 35 shown in FIG. 2. The combined stream 66 is then deposited in cavities 44 to overlay the dusting layer and form the primary layer 36 comprising a combination of hydrophilic fiber material and discrete particles of absorbent gelling materials.

The airlaying module 40 includes a plurality of vacuum chambers (not shown) within the interior of the foraminous forming drum 42. Each of the vacuum chambers is connected to a suitable source of vacuum (not shown). Entrainment air for forming air-entrained streams of fibers 62 and 63 is drawn through the foraminous forming drum 42 by the vacuum maintained in the vacuum chambers within the interior of the forming drum 42. U.S. Pat. No. 4,592,708 issued Jun. 3, 1986 to Feist et al. and above referenced U.S. Pat. Nos. 4,908,175 and 4,765,780 are incorporated herein by reference for the purpose of showing a suitable airlaying module 40 for use with the present invention.

FIG. 3 shows one embodiment of the present invention. Discrete particles 38 of absorbent gelling material are directed from a supply source (not shown) to branched conduit 307 as indicated by arrow 305. A valve associated with branched conduit 307 is movable from a first position 309A to a second position 309B shown in phantom.

In a first operating mode the valve is positioned in the first position 309A so that the discrete particles 38 of absorbent gelling material are directed to and accumulated in a filter receiver vessel 300. Air in filter receiver vessel 300 is removed through a filter 330 and air conduit 320 by a suitable vacuum source 340.

The particles in filter receiver vessel 300 are gravity fed to the particle metering device 80. The metering device 80 delivers a predetermined mass of discrete particles 38 per unit time. The metering device 80 can include a hopper 84, screw feeder 86, and scale 88. A suitable metering device is an Acrison Volumetric Feeder, Model No. 405-105X-F, available from Acrison, Inc. of Moonachie, N.J.

The metered quantity of particles 38 is delivered by screw feeder 86 to a funnel receiver 91 and directed to an eductor 90. Eductor 90 entrains the metered quantity of particles 38 within a motive air flow to provide the air-entrained supply stream 82 of discrete particles. The motive air flow can be provided by a suitable blower 92. A suitable eductor 90 is a Fox Eductor, Model No. 612046, available from the Fox Valve Development Corporation, of Dover, N.J. A suitable blower 92 is a Fuji Blower, Model VFC503A, available from the Fuji Electric Corporation of America, Lincoln Park, N.J.

The air-entrained supply stream 82 of discrete particles is carried by a particle carrying conduit, which can comprise a particle delivery chute 94 and the delivery nozzle 120. The delivery chute 94 carries the supply stream 82 of discrete particles to the mask delivery nozzle 120. The mask delivery nozzle 120 directs the supply stream 82 to form an acute included angle A with the diverting surface 110 of the mask 100. The particles 38 in the first intermittent stream 103 passing through the mask 100 are combined with the air-entrained stream of fibers 62 in the diverging duct 65, and directed to the foraminous forming drum 42 by the hood 50.

The particles 38 in the second intermittent stream 105 are deflected by the diverting surface 110 of the mask 100. The momentum of the particles in the second intermittent stream 105 carries the particles in a predetermined direction (vertically downward in FIG. 3) to enter a conduit 410. The deflected particles are carried in the conduit 410 for recycling. In the embodiment shown in FIG. 3, the conduit 410 carries the diverted particles to vacuum receiving chamber

400. A vacuum source 450 provides an airflow through a particle filter 430 for drawing the particles in conduit 410 into the vacuum receiving chamber 400. A suitable vacuum source 450 is commercially available from the Buffalo Forge Company of Buffalo, N.Y. as Model No. 3RE.

The recycled particles accumulate in the vacuum receiving chamber 400 during the first operating mode. In a second operating mode, the valve associated with branched conduit 307 is moved to position 309B, thereby blocking the flow 305 of discrete particles from the supply source. With the valve in position 309B, a rotary air lock 420 positioned under the vacuum receiving chamber 400 is rotated to gravity feed at least a portion of the accumulated recycled particles in chamber 400 into a pick-up pan 490. The rotary air lock 420 permits the accumulated recycled particles in chamber 400 to enter the pick-up pan 490, while maintaining the vacuum in chamber 400 provided by the vacuum source 450. A suitable rotary air lock 420 is available from Prater Industries, Inc. of Chicago, Ill. as Model No. PAV-6C. A blower 492 is activated to provide a motive air flow for carrying the recycled particles entering pick-up pan 490 through a conduit 493. The recycled particles carried in conduit 493 pass through branched conduit 307 and into the filter receiver vessel 300.

The apparatus is returned to the first operating mode by deactivating the rotary air-lock 420 and the blower 492, and by moving the valve associated with the branched conduit 307 to position 309A. The transition between the first and second operating modes can be made at a predetermined time-interval, or alternatively, can be made based on the amount of recycled particles accumulated in the chamber 400.

Figure 4:
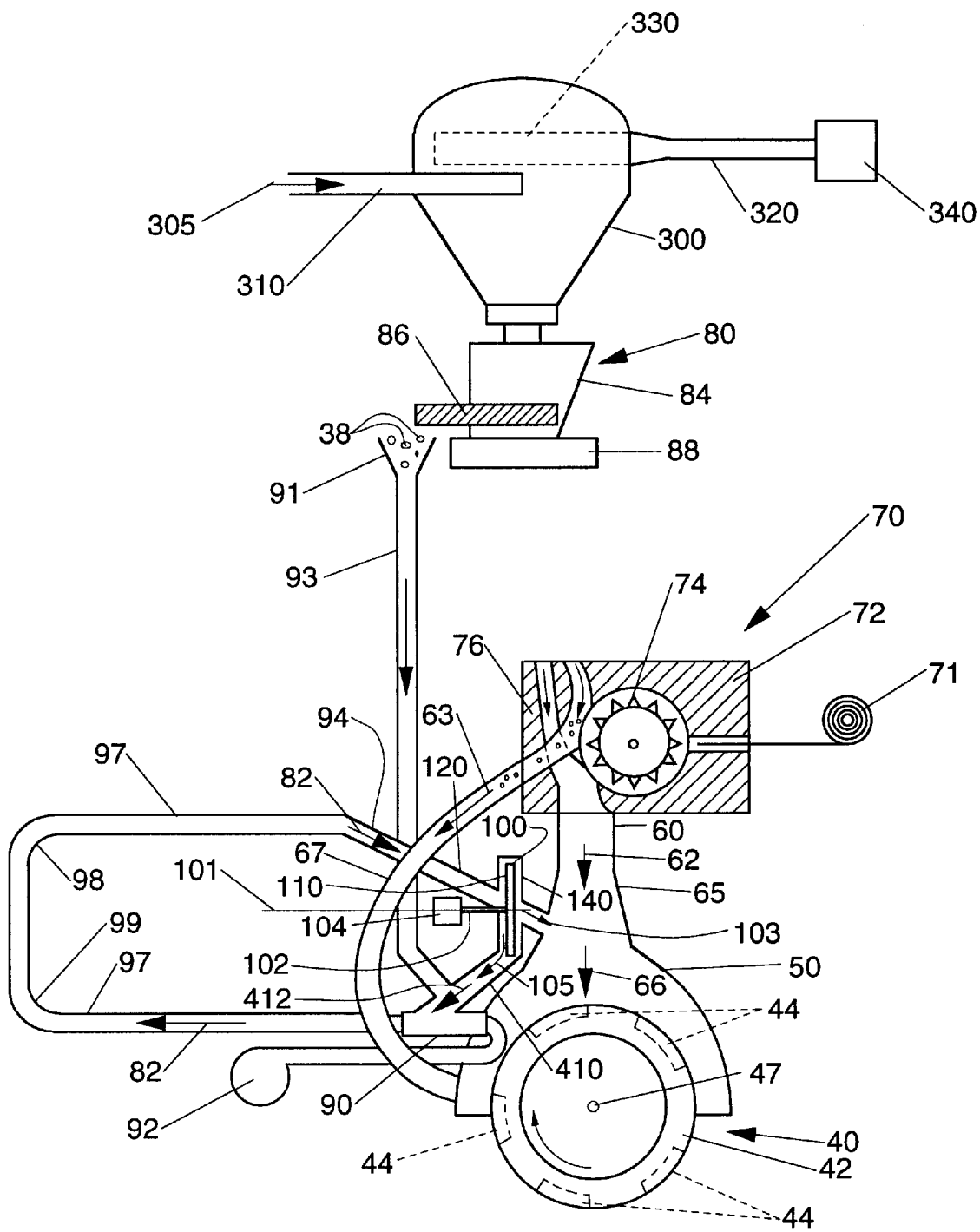
FIG. 4 is a schematic illustration of an apparatus according to an alternate embodiment of the present invention having an alternative particle recycling arrangement.

FIG. 4 shows an alternative embodiment of the present invention for providing an air-entrained stream 82 of discrete particles and recycling the second intermittent stream 105 of particles not combined with the air-entrained stream of fibers 62. Discrete particles 38 of absorbent gelling material are carried by a conduit 310 from a supply source (not shown) to a filter receiver vessel 300 as indicated by arrow 305. A vacuum source 340 provides a motive air flow through a particle filter 330 and a conduit 320 for carrying the discrete particles into the vessel 300.

The particles in filter receiver vessel 300 are gravity fed to the particle metering device 80. The metering device 80 delivers a predetermined mass of discrete particles per unit time. The metering device 80 can include a hopper 84, screw feeder 86, and scale 88 as described above with reference to FIG. 3. The metered quantity of particles is delivered by screw feeder 86 to a funnel receiver 91 and carried by a conduit 93. The conduit 93 empties the metered quantity of discrete particles into the conduit 410, so that the metered quantity of discrete particles is combined with the second intermittent stream 105 of particles deflected by the mask 100. Both the conduit 93 and the conduit 410 can be inclined vertically downward to provide gravity assisted feeding of the metered quantity of particles and the deflected particles. The combined stream of metered and deflected particles is indicated by arrow 412 in FIG. 4.

The conduit 410 directs the combined stream of particles 412 to an eductor 90. The eductor 90 and a blower 92 entrain the combined stream of particles 412 within a motive air flow to provide the air-entrained supply stream 82 of discrete particles. A suitable eductor 90 is a Fox Eductor, Model No. 300-SCE-SS available from the Fox Valve Development Corporation. A suitable blower 92 is a Cooper/Sutorbilt Blower, Model 3M Legend, also available from the Fox Valve Development Corporation. The air-entrained supply stream 82 of discrete particles is carried by a conduit 97 to a particle carrying conduit comprising the particle delivery chute 94 and the mask delivery nozzle 120. The chute 94 directs the supply stream 82 of particles to the mask delivery nozzle 120.

The conduit 97 can have a circular cross-section with an inner diameter of about 6.0 cm (2.4 in.) and can include bends 98 and 99 having a radius at the center of the duct cross-section of at least about 30 cm (12 in.). The bends 98, 99 and the particle delivery chute 94 preferably lie in a common plane, which common plane is parallel to the plane of FIG. 4 and passes through the center of the forming cavities 44. The bends 98, 99 help to center the particles in the conduit 97 in this common plane. Positioning the bends 98, 99 and the chute 94 in this common plane aids in aligning the first intermittent stream 103 of particles passing through the mask 100 within the forming cavities 44.

The embodiment shown in FIG. 4 provides a metered quantity of discrete particles, combines the metered quantity of discrete particles with the second intermittent stream 105 of discrete particles deflected by the mask, entrains the combined metered and deflected discrete particles in an air flow to form an air-entrained supply stream 82, and directs the air-entrained supply stream 82 of discrete particles to form an acute included angle A with the mask 100.

The embodiment shown in FIG. 4 is advantageous in that it does not require the two mode operation of FIG. 3. The embodiment shown in FIG. 4 is also advantageous because the discrete particles deflected by the mask 100 for recycling are continuously mixed with freshly metered discrete particles from the metering device 80. Such an arrangement provides recycling of the discrete particles which is independent from the supply source (not shown) of the discrete particles. Therefore, the embodiment shown in FIG. 4 can be easily adapted to different production sites having different types or arrangements of supply sources of the discrete particles.

In one embodiment of the present invention, the air-entrained stream of fibers 62 can comprise about 1 to about 24 kg/minute of fiber carried in an air stream having a velocity of about 610 meter/minute (2,000 feet/minute) to about 4,600 meter/minute (15,000 feet/minute) and an air flow rate of about 3.8 cubic meters/minute (136 cubic feet/minute) to about 29 cubic meters/minute (1,020 cubic feet/minute). The air-entrained stream of particles 82 can comprise about 1 kg/minute to about 20 kg/minute of particles carried in an airstream having a velocity of about 610 meter/minute (2,000 feet/minute) to about 3,700 meter/minute (12,000 feet/minute) and an air flow rate of about 1.7 cubic meters/minute (60 cubic feet/minute) to about 10.2 cubic meters/minute (360 cubic feet/minute).

Figure 5:
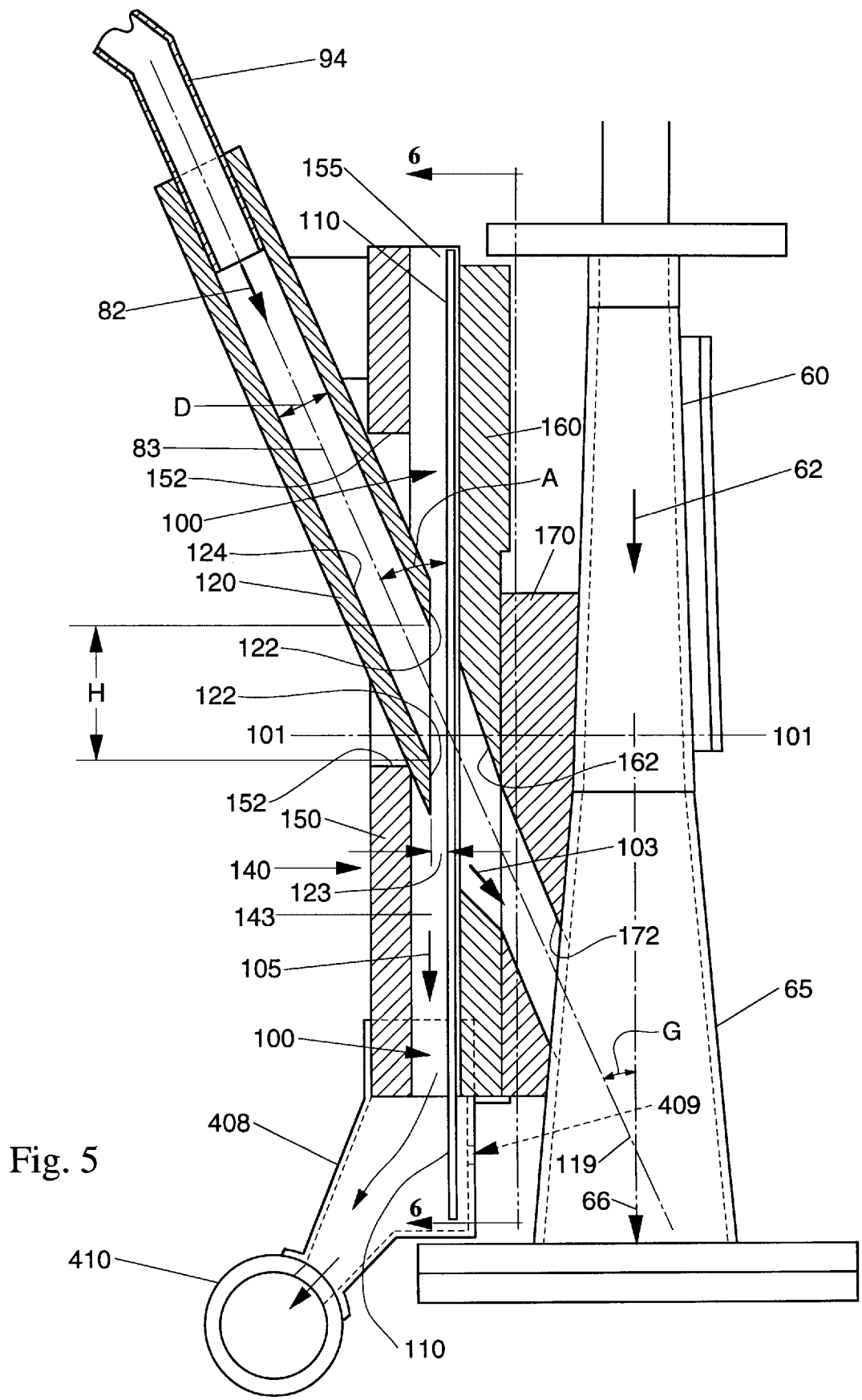
FIG. 5 is a cross-sectional side view of the mask supported in an enclosure and the mask delivery nozzle.
Figure 6:
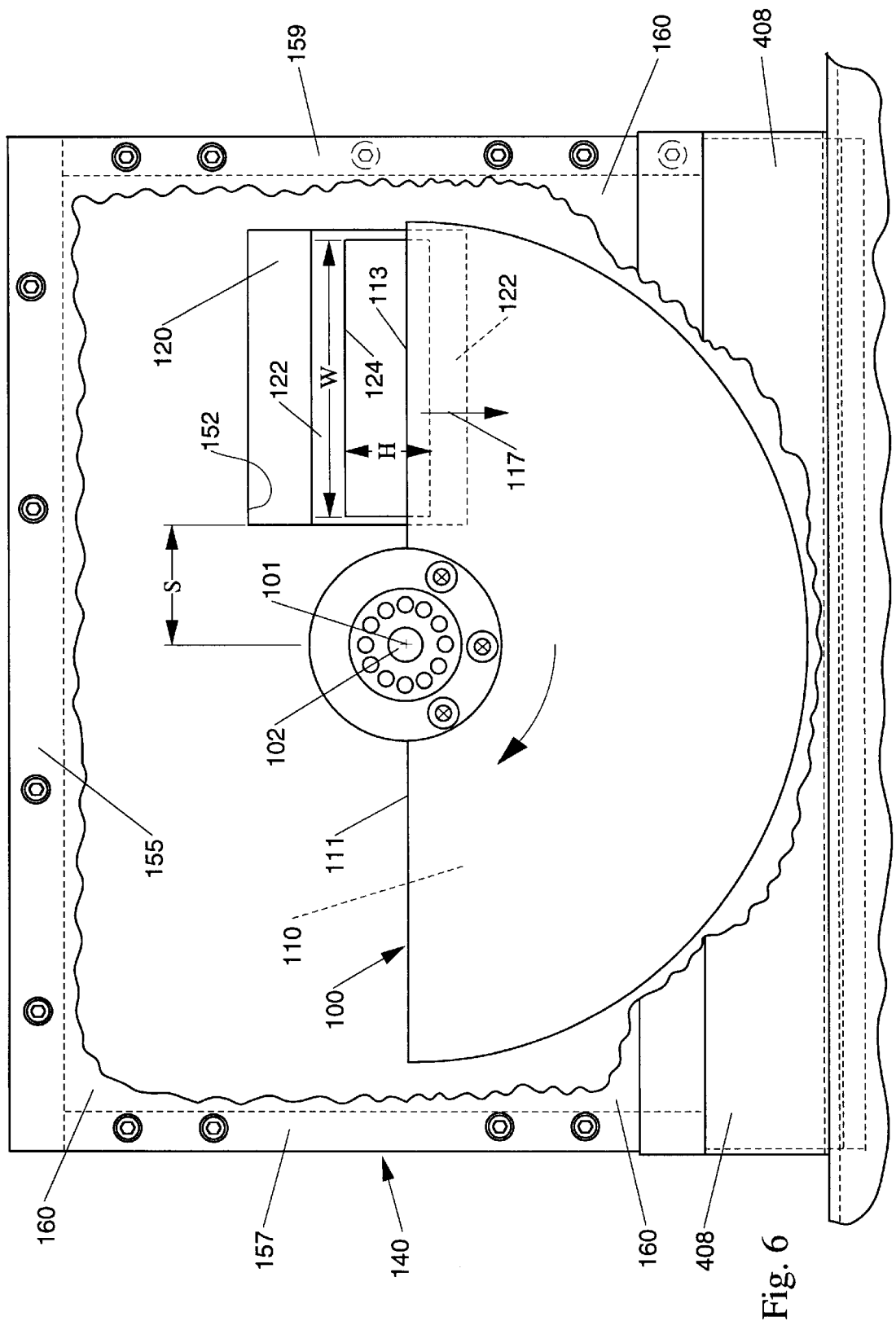
FIG. 6 is a view taken along line 6—6 in FIG. 5 showing the mask supported in the enclosure, with the enclosure partially cut-away.
Figure 7:
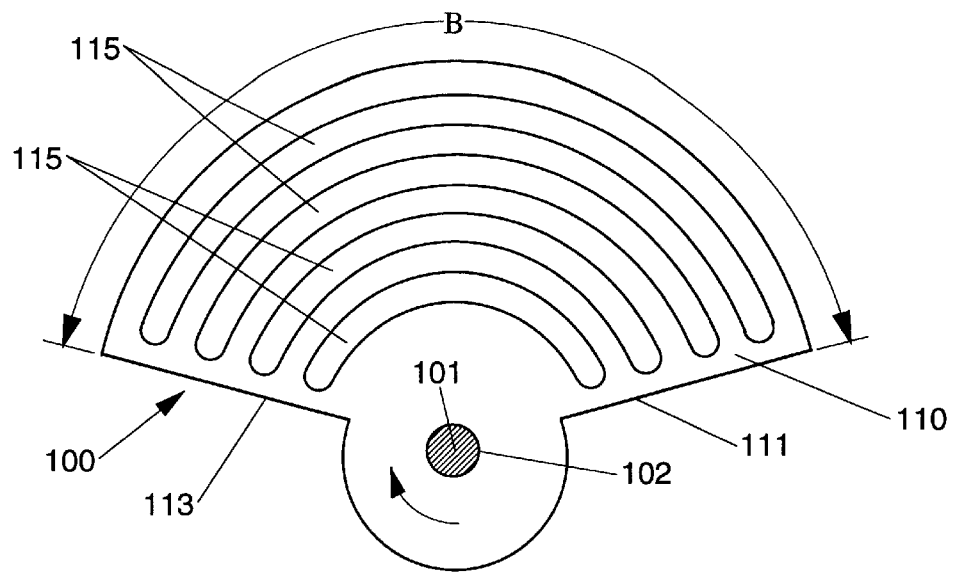
FIG. 7 is a plan view of a mask having apertures in the diverting surface.
Figure 9:
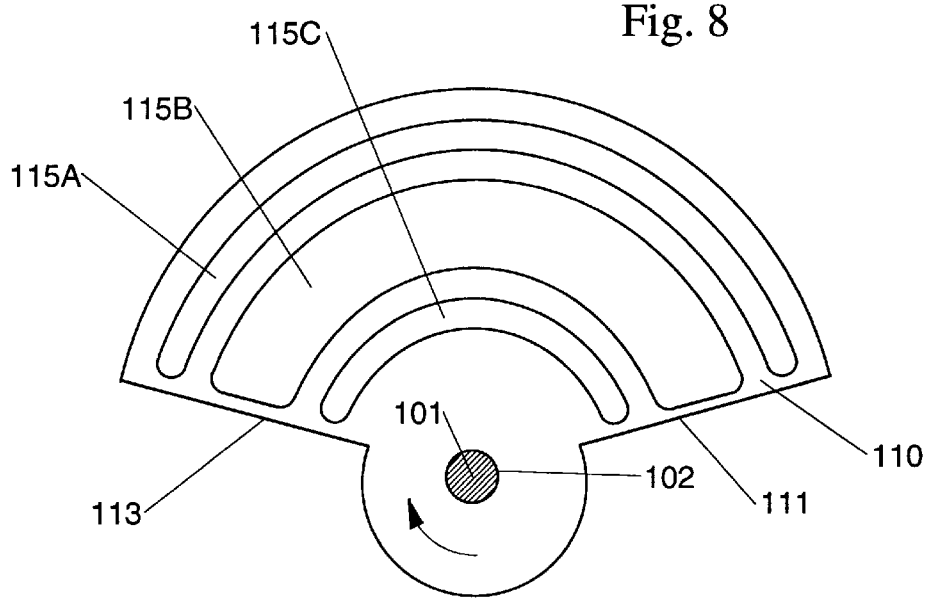
FIG. 9 is a plan view of a mask having apertures with different radial widths for forming a lateral distribution of particles shown in FIG. 11.

FIG. 5 is a cross-sectional side view of the mask 100 and the mask delivery nozzle 120. The mask 100 is shown disposed within an enclosure 140. FIG. 6 is a front elevation view of the enclosure 140 taken along line 6—6 in FIG. 5, with the enclosure 140 partially cut-away. FIGS. 7 and 9 show different embodiments of the mask 100.

Referring back to FIG. 5, the mask delivery nozzle 120 can be an extension of the particle delivery chute 94. The mask delivery nozzle 120 directs the air-entrained supply stream 82 of discrete particles to form an acute included angle A with the diverting surface 110. The term "acute angle" refers to an angle less than ninety (90) degrees. The angle A is measured from the imaginary axis 83 along which the air-entrained stream of discrete particles 82 is directed, rather than from the surface of the supply stream 82, which may diverge or converge slightly with respect to the axis 83 of the stream 82. If the axis 83 is curved, the angle A is measured from the tangent of the axis 83 where the axis 83 intersects the plane of the diverting surface 110.

Referring to FIGS. 5 and 6, the mask 100 is preferably supported for rotation in a cavity 143 within an enclosure 140. The enclosure 140 isolates the mask 100 and the particle streams 82, 103, and 105 from surrounding conditions which might otherwise adversely affect the formation of the particle stream 103. In particular, the cavity 143 in the enclosure 140 is closed to surrounding atmospheric conditions to maintain the air flows which carry particle streams 82, 103, and 105. The enclosure 140 also serves as a containment structure for holding particle dust.

The enclosure 140 includes an upstream wall 150, a downstream wall 160, a top wall 155, and side walls 157, 159. A trough 408 can be joined to the bottom of the enclosure 140 for receiving particles deflected by the diverting surface 110. The trough 408 can include one or more vents 409 for providing an air passage into the trough 408 and the conduit 410. Such an air passage provides air for carrying particles in the conduit 410.

The upstream and downstream wall 150 and 160 are parallel to and closely spaced from the mask 100. The spacing between the upstream wall 150 and the mask 100 is preferably about 1.1 cm (0.43 inch). The spacing between the downstream wall 160 and the mask 100 is preferably no more than about 0.3 cm (0.12 inch). The spacing between the upstream wall 150 and the mask 100 is greater than the spacing between the downstream wall 160 and the mask 100 in order to provide a flow path for the deflected intermittent stream 105 of discrete particles.

The mask delivery nozzle 120 extends through an aperture 152 in the upstream wall 150. The delivery nozzle 120 can have an elongated internal passage 124 oriented radially from the axis 101 of the mark 100. The elongated passage 124 can have a height D of about 1.7 cm (0.69 inch) and a width W (FIG. 6) of about 9.4 cm (3.7 inch). The delivery nozzle 120 has a beveled face 122 parallel to the mask 100 and positioned intermediate the upstream wall 150 and the mask 100 to provide close spacing of the nozzle 120 from the diverting surface 110. The beveled face 122 is preferably spaced a distance 123 from the mask 100 of about 0.8 cm (0.3 inch) to precisely direct the air-entrained supply stream 82 of discrete particle against the diverting surface 110.

The downstream wall 160 includes a downstream passageway 162 for receiving the first intermittent stream 103 of particles passing through the mask. The passageway 162 can converge in the downstream direction from an upstream entrance enlarged with respect to the internal passageway 124, as shown in FIG. 5. The enlarged upstream entrance of the passageway 162 aids in capturing all particles passing through the mask 100.

An adapter 170 joins the downstream wall 160 to the diverging duct 65. A passageway 172 extending through the adapter 170 provides a flowpath through which the first intermittent stream 103 of discrete particles enters the diverging duct 65. In a preferred embodiment the axis 119 of the first intermittent stream 103 of particles forms an angle G of about 10 degrees to about 50 degrees with the air-entrained stream of fibers 62, and most preferably about 24 degrees.

Figure 8:
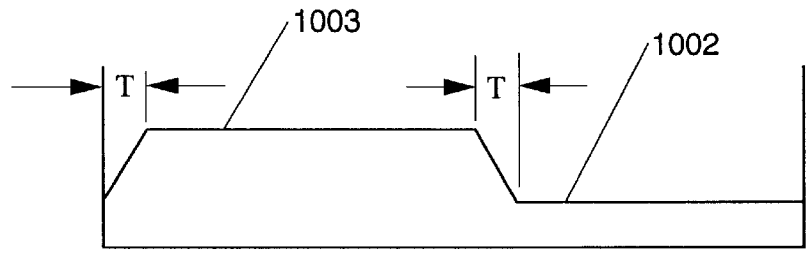
FIG. 8 is a schematic illustration of a longitudinal distribution of particulate material in an absorbent core.

FIG. 8 shows a longitudinal distribution of absorbent gelling material particles in an absorbent core, as measured along the longitudinal axis 21 of the diaper 20 shown in FIG. 1. The distribution includes a relatively high basis weight region 1003, a relatively low basis weight region 1002, and transition regions T between the high and low basis weight regions 1002 and 1003. As the mask 100 rotates about axis 101, the air-entrained supply stream 82 of particles is intermittently interrupted by the diverting surface 110 and split into the first and second intermittent streams 103 and 105.

In one embodiment the mask 100 can rotate once for each fibrous web 41 formed on drum 42, in which case, the distribution shown in FIG. 8 corresponds to the distribution of absorbent particles along the length of one shaped core component 34. In other embodiments it may be desirable to rotate the mask 100 more or less than one revolution for each fibrous web 41 formed on drum 42.

As shown in FIG. 7, the diverting surface 110 can comprise a circular sector, such as a sector of a disk. The diverting surface 110 can subtend an angle B from a leading edge 111 to a trailing edge 113. The relatively high basis weight region 1003 corresponds to those angular positions of the mask 100 where relatively little, or none, of the supply stream 82 of discrete particles is deflected by the diverting surface 110. The relatively low basis weight region 1002 corresponds to those angular positions of the mask 100 where a relatively large percentage, or all, of the stream of particles 82 is deflected by the diverting surface 110. The transition regions T correspond to those angular positions of the mask 100 where the leading and trailing edges 111 and 113 intersect the supply stream 82 of particles.

The mask 100 is supported for continuous motion with respect to the air-entrained stream of particles 82 to avoid the inertial forces and design and control complexities associated with an apparatus that accelerates and decelerates between two stationary positions. In a preferred embodiment of the present invention, the mask 100 is supported for continuous rotation about the axis 101. In one preferred embodiment, the mask 100 is fixed to shaft 102, and shaft 102 is rotatably supported on bearings (not shown). The mask 100 is preferably rotated at a substantially constant angular velocity to avoid inertial forces associated with angular acceleration and deceleration. By a "substantially constant angular velocity" it is meant that the mask 100 is rotated to maintain an angular velocity of within about 2 percent of a baseline angular velocity, with it being understood that the rotational speed of the mask 100 may be temporarily increased or decreased by no more than about 2 percent of the baseline angular velocity in order to maintain a desired phasing of the angular position of the mask 100 with the angular position of the foraminous forming drum 42.

In an alternative embodiment (not shown), the mask 100 can comprise an endless belt having an apertured surface. The endless belt can be driven by a motor or other driving means at a generally constant speed, and the particle nozzle 120 can direct the air-entrained stream 82 of discrete particles to form an acute included angle A with the belt surface. The apertured belt surface splits the air-entrained supply stream 82 of discrete particles into the first stream 103 passing through the apertures in the belt surface, and the second stream 105 deflected by the belt surface.

Applicants have found that directing the air-entrained stream of discrete particles 82 to form an acute included angle A with the diverting surface 110 provides benefits with respect to pulsing and recycling the discrete particles. A supply stream 82 of particles directed normal to the diverting surface 110 could be reflected backward, into the incoming particle stream 82. Such reflected particles could disrupt the incoming particle stream, thereby increasing the transition regions T, or otherwise complicating the formation of a well defined intermittent stream of particles passing through the mask 100. Such a well defined intermittent stream is desirable to provide distinct high and low basis weight regions 1003 and 1002. In addition, such backward reflected particles can be scattered in random directions, thereby complicating recycling of the discrete particles deflected by the diverting surface 110.

According to the present invention, when the supply stream 82 of discrete particles is directed to form an acute included angle A with the diverting surface 110, the deflected particles in the second intermittent stream 105 will have a component of momentum parallel to the diverting surface 110. This component of momentum parallel to the diverting surface will carry the deflected particles to a predetermined location. Referring to FIG. 5, the momentum of the deflected particles in the first intermittent stream 105 carries the deflected particles to a trough 408 connected to the bottom of the enclosure 140. The trough 408 is joined to the conduit 410 to provide a flow path for recycling of the deflected particles.

As the angle A is decreased, the component of momentum of the particles parallel to the diverting surface 110 will increase. The angle A is preferably less than about sixty degrees, and more preferably less than about 45 degrees to provide a relatively large component of particle momentum parallel to the diverting surface 110. However, without being limited by theory, it is believed that the angle A should be at least about 20 degrees, and can be about 24 degrees to be generally equal to the angle G. Referring to FIGS. 5 and 6, the depth D of the internal passageway 124 has a projected height H on the diverting surface 110 which is approximately equal to the depth D divided by the sine of angle A. For a fixed depth D, the projected height H will increase as the angle A is decreased, resulting in a longer transition region T in FIG. 8. In one embodiment of the present invention, the angle A can be between about 20 to about 30 degrees to provide an adequate component of particle momentum parallel to the diverting surface 110 without creating an unacceptably long transition region T.

Referring to FIG. 6, a portion of the downstream wall 160 of the enclosure 140 is cutaway to show the mask 100 supported for rotation on the shaft 102. FIG. 6 shows the mask 100 in a position corresponding to a transition region T, with the trailing edge 113 intersecting the supply stream 82 of discrete particles. It is generally desirable to decrease the longitudinal length of the transition region T in order to provide more precise placement of the absorbent gelling material in the absorbent core. The longitudinal length of the transition region T decreases with increasing radial offset S of the internal passageway 124 from the axis 101 of the mask 100. The transition region T increases with increasing depth D and with decreasing included angle A. For a mask rotational speed of about 600 RPM, an angle A between about 20 and 40 degrees, and the width W and depth D listed above, the offset S can be about 4.8 cm (1.9 inch) to provide an acceptable transition region T of about 42 degrees of rotation of the mask 100, or about 12 percent of the total longitudinal distribution shown in FIG. 8 corresponding to one rotation of the mask 100.

The nozzle 120 directs the supply stream 82 to have a velocity component out of the plane of FIG. 6, and a velocity component directed vertically downward. The mask rotates clockwise in FIG. 6, as viewed from the downstream side of the mask, and has a vertically downward velocity component 117 as it intersects the supply stream 82. It is desirable to rotate the mask 100 such that the mask 100 intersects the supply stream 82 with a velocity component 117 parallel to a velocity component of the supply stream 82. Parallel motion of the mask 100 with a velocity component of the supply stream 82 reduces the chance that the leading edge 111 or the diverting surface 110 will reflect particles backward into the incoming particle stream 82.

Referring again to FIG. 7, the diverting surface 110 can have one or more apertures, such as circumferentially extending slots 115. The slots 115 can be radially spaced apart and radially aligned as shown in FIG. 7. Two apertures are considered to be radially aligned if a radial line drawn through the axis 101 intersects both apertures. The radially spaced apart and radially aligned circumferentially extending slots 115 shown in FIG. 7 provide a particle distribution in the low basis weight region 1002 which is generally uniform in the lateral direction (parallel to the lateral centerline 23 of the diaper 20), and which has a basis weight greater than or equal to zero and less than the basis weight in the relatively high basis weight region 1003.

Figure 11:
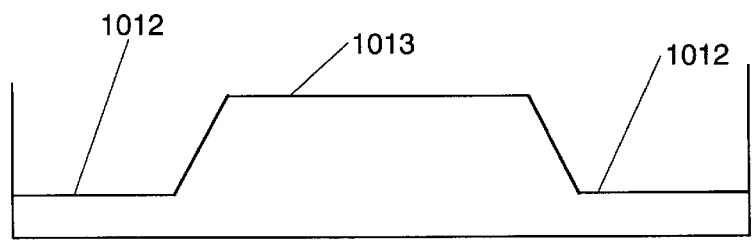
FIG. 11 is a schematic illustration of a lateral distribution of particulate material in an absorbent core.

FIG. 9 shows an embodiment of the mask 100 in which the radial width of radially spaced apart and radially aligned apertures, such as the circumferential slots 115A, 115B, and 115C, varies as a function of radial position of the slots 115. Such a variation in radial width of the slots 115 can provide a lateral distribution of particles in the core perpendicular to the longitudinal axis 21. Such a lateral variation is shown in FIG. 11. For instance, the variation in radial width shown in FIG. 9 can provide a lateral particle distribution having a relatively high basis weight region 1013 along the longitudinal centerline 21 of the diaper 20 and relatively low basis weight regions 1012 laterally outward of the region 1013. Each slot 115 can have a constant radial width, or alternatively, one or more of the slots 115 can have a variable radial width. In an alternative embodiment, circular apertures having a diameter that varies as a function of radius can be used to provide a lateral variation in basis weight. Of course, other aperture shapes can also be used.

In an alternative embodiment (not shown), the diverting surface 110 can comprise an uninterrupted surface having no apertures for providing a region 1002 having no absorbent gelling material. In yet another embodiment the diverting surface 110 can extend through 360 degrees and include a circumferentially varying pattern of apertures for providing two or more regions of different basis weight in the longitudinal direction. The mask 100 can be formed from any suitable material which can resist abrasion, including, but not limited to stainless steel.

In the embodiment shown in FIG. 5, the particle nozzle 120 directs the air-entrained stream of particles 82 with a vertically downward velocity component. In addition, the diverting surface 110 may be inclined with respect to the horizontal plane and may rotate about an axis 101 inclined with respect to the vertical axis. As shown in FIG. 5, the axis of rotation 101 of the mask 100 can be horizontal, and the diverting surface 110 can be vertical. Such an arrangement has the advantage that gravity assists in directing the deflected particles in the second intermittent particle stream 105 into the trough 408 and the conduit 410.

Figure 10:
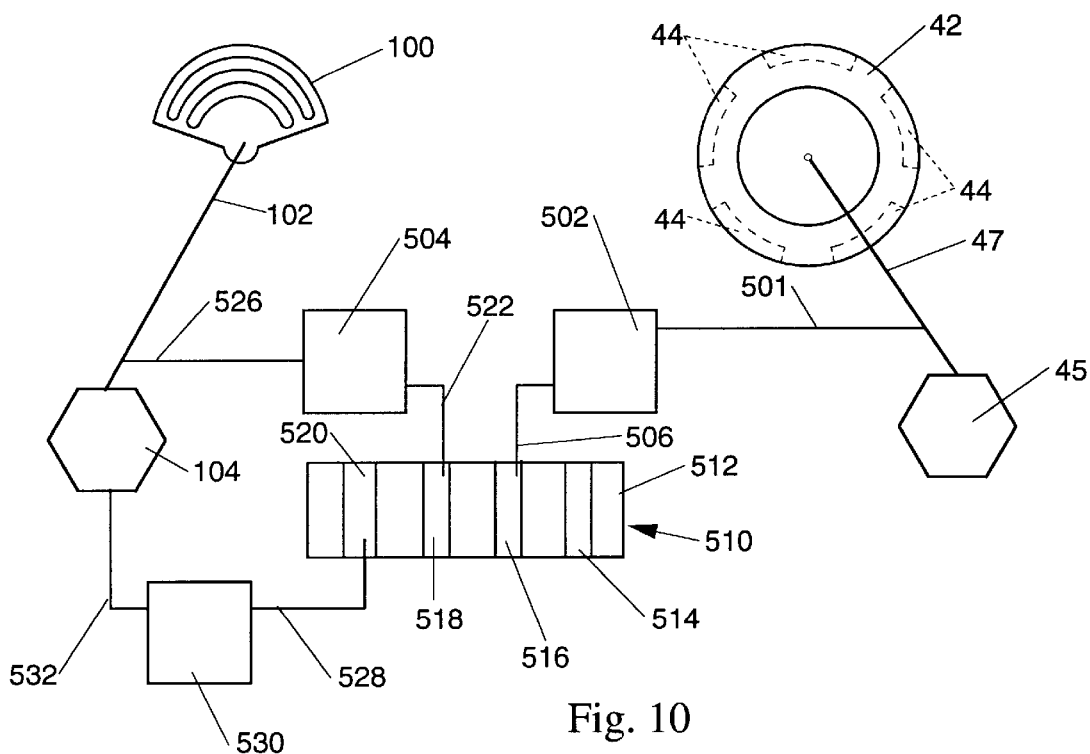
FIG. 10 is a schematic illustration of a means for providing phasing of the position of the mask with the position of the foraminous forming element.

FIG. 10 schematically illustrates a means for maintaining a desired phasing of the angular position of the mask 100 with the angular position of the foraminous forming drum 42 in order to maintain the desired longitudinal distribution of absorbent gelling material in the absorbent pads formed on the forming drum 42. The means for maintaining the desired phasing includes a master position resolver 502, a slave position resolver 504, a computer 510, and a motor controller 530.

The mask 100 is driven directly, or indirectly, by a motor 104 through a drive train which includes the shaft 102. The motor 104 can be a brushless DC electric motor such as is available from the Reliance Electric Company of Cleveland, Ohio. Forming drum 42 is driven directly or indirectly by a motor 45 through a drive train which includes shaft 47. The master position resolver 502 detects the angular position of shaft 47, or a shaft geared to shaft 47, as indicated by connection 501. The master resolver 502 provides a signal representing the position of shaft 47 to the computer 510 via data line 506. The slave position resolver 504 detects the angular position of the shaft 102, or a shaft geared to the shaft 102, as indicated by connection 526. The slave position resolver 504 provides a signal representing the position of shaft 102 to the computer 510 via data line 522. Using the input signals from data lines 506 and 522, the computer 210 determines and sends a proportionate analog voltage signal to the motor controller 530 via the data line 528. The motor controller 530 provides a speed signal to the motor 104 via data line 532 in order to speed or slow the motor 104 as needed to maintain the angular position of the mask 100 phased with respect to the angular position of the forming drum 42.

In one embodiment, the mask 100 makes one revolution for each absorbent core, or five rotations for each rotation of a forming drum 42 having five forming cavities 44. Both the master and the slave resolvers 502 and 504 are assigned 4096 counts per revolution. The computer 510 compares the number of counts received from each of the resolvers in a given time period to determine a position error of the mask 100 relative to the forming drum 42.

Suitable master and slave position resolvers 502 and 504 are available from the Reliance Electric Company of Cleveland, Ohio under the model designation 57C360 or 57C361. A suitable computer 510 is available from the Reliance Electric Company under the name Reliance AUTOMAX DCS (distributed control system), and includes a power supply 512, a Reliance Model 7010 CPU 514, a master resolver card 516, a slave resolver card 518, and an analog output card 520. A suitable motor controller 530 is a Reliance Model HR2000 motor controller set to "speed mode." The computer 510 can be configured and programmed according to the AUTOMAX Programming Reference Manual, Version 2.0; the AUTOMAX System Operation Manual, Version 3.0; and the AUTOMAX Hardware Reference Manual. In an alternative embodiment, the mask 100 and the forming drum 42 can be coupled mechanically to maintain the desired angular phasing, such as with a timing belt, timing chain, or gear train.

While particular embodiments of the present invention have been illustrated and described, it would be obvious to those skilled in the art that various changes and modifications can be made without departing from the spirit and scope of the invention. For instance, in the embodiments shown, the particles in one of the intermittent streams 103, 105 are directed to a web, and the particles in the other stream are recycled. Alternatively, the particles in both intermittent streams can be directed for laydown on different webs, or on different portions of the same web. It is intended to cover, in the appended claims, all such modifications and intended uses.

What is claimed is:

1. An apparatus for forming an intermittent stream of discrete particles for application to a fibrous web, the apparatus comprising:

a particle carrying conduit for carrying a supply stream of the discrete particles;

a mask continuously rotating about an axis, the mask having a diverting surface for splitting the supply stream of discrete particles into a first intermittent stream passing through the mask and a second intermittent stream deflected by the diverting surface;

wherein the particle carrying conduit is positioned relative to the diverting surface to direct the supply stream of discrete particles to form an acute included angle with the diverting surface; and wherein the diverting surface includes apertures having a radial width which varies as a function of the radial position of the apertures.

2. The apparatus of claim 1 wherein the supply stream of discrete particles forms an included angle of less than 60 degrees with the diverting surface.

3. The apparatus of claim 2 wherein the supply stream of discrete particles forms an included angle of about 20 to about 30 degrees with the diverting surface.

4. The apparatus of claim 1 wherein the axis of rotation of the mask is inclined with respect to a vertical axis.

5. The apparatus of claim 4 wherein the mask has a vertical diverting surface.

6. The apparatus of claim 5 wherein the supply stream of particles is directed with a vertically downward velocity to form an acute included angle with the diverting surface.

7. The apparatus of claim 1 wherein the diverting surface includes at least two radially spaced apart and radially aligned apertures.

8. An apparatus for forming an airlaid fibrous web having discrete particles dispersed through a predetermined portion of the web, the apparatus comprising:

airlaying means having a foraminous forming element for forming an airlaid fibrous web;

means for forming an air-entrained stream of fibers;

means for forming an air-entrained supply stream of discrete particles;

a mask continuously rotating about an axis, the mask having a diverting surface for splitting the supply stream of discrete particles into a first intermittent stream of particles passing through the mask and a second intermittent stream of particles deflected by the diverting surface;

means positioned relative to the diverting surface for directing the supply stream of discrete particles to form an acute included angle with the diverting surface;

means for combining the air-entrained stream of fibers with one of the intermittent streams of particles to form a combined stream comprising an intermittent stream of particles within a continuous stream of fibers;

means for directing the combined stream of fibers and particles to the forming element of the air laying means; and means for phasing the position of the mask with the position of the web.

9. The apparatus of claim 8 comprising means for combining the air-entrained stream of fibers with the first intermittent stream of particles.

\* \* \* \* \*